(12) United States Patent
Colin et al.

(10) Patent No.: US 7,097,623 B2
(45) Date of Patent: Aug. 29, 2006

(54) BIOLOGICAL SAMPLING METHOD

(75) Inventors: Bruno Colin, Marcy l'Etoile (FR); Cécile Jaravel, Marcy l'Etoile (FR); Marie Privat, Saint Romain en Gal (FR)

(73) Assignee: Biomerieux S.A., Marcy l'Etoile (FR)

( * ) Notice: Subject to any disclaimer, the term of this patent is extended or adjusted under 35 U.S.C. 154(b) by 434 days.

(21) Appl. No.: 10/640,646

(22) Filed: Aug. 14, 2003

(65) Prior Publication Data

US 2004/0048393 A1   Mar. 11, 2004

Related U.S. Application Data

(63) Continuation of application No. 09/675,648, filed on Sep. 29, 2000, now Pat. No. 6,641,545, which is a continuation of application No. PCT/FR99/00728, filed on Mar. 29, 1999.

(30) Foreign Application Priority Data

Apr. 1, 1998   (FR) .................................. 98 04144
Jun. 22, 1998  (FR) .................................. 98 07884

(51) Int. Cl.
  *A61B 5/00*    (2006.01)
  *B65D 81/00*   (2006.01)
  *G01N 1/10*    (2006.01)
(52) U.S. Cl. ..................... 600/579; 436/180
(58) Field of Classification Search ................ 600/573, 600/576, 578, 579; 604/317–335; 73/863, 73/864, 863.01, 863.03, 863.32, 863.51, 73/864.01, 864.11, 864.13, 864.15, 864.34, 73/864.61, 864.62; 137/1, 557; 436/180

See application file for complete search history.

(56) References Cited

U.S. PATENT DOCUMENTS

| 3,982,438 A | 9/1976 | Byrd ......................... 73/425.6 |
| 4,846,003 A | 7/1989 | Marquiss ................ 73/864.24 |
| 5,723,795 A | 3/1998 | Merriam ...................... 73/863 |
| 6,045,541 A | 4/2000 | Matsumoto et al. ........ 604/313 |

FOREIGN PATENT DOCUMENTS

| EP | 0 341 438 A | 11/1989 |
| EP | 0 571 100 A | 11/1993 |

*Primary Examiner*—Max F. Hindenburg
*Assistant Examiner*—Brian Szmal
(74) *Attorney, Agent, or Firm*—James C. Lydon

(57) ABSTRACT

A method for drawing a biological sample using a suction-discharge device, such as a manual or automatic pipette, built into an automated device or not. A method for detecting the free surface of a biological sample and/or solid, a sample drawing device such as a pipette and a device for detecting the free surface of a biological sample or a solid are also disclosed. This method includes actuating a means causing a pressure variation or an air flow within the suction-discharge device, positioning the lower free end of the device in such a way so that it becomes flush with a free surface of the biological sample, measuring an overpressure within the suction-discharge device, and sampling a quantity of the sample by suction using the device. The invention finds a preferable application in the field of automatic analyzers.

2 Claims, 6 Drawing Sheets

BIOLOGICAL SAMPLING METHOD

This application is a continuation of application Ser. No. 09/675,648, filed Sep. 29, 2000, now U.S. Pat. No. 6,641,545 which is a continuation of International application PCT/FR99/00728, filed Mar. 29, 1999, and claims priority of French Application No. 98/07884, filed Jun. 22, 1998, and French Application No. 98/04144, filed Apr. 1, 1998.

BACKGROUND OF THE INVENTION

1. Field of the Invention

The present invention relates to a method for drawing a biological sample by means of a suction-discharge device, such as a pipette, either manual or automatic, and built into an automated device or not. It also relates to a process used to detect the free surface of a biological sample or a solid by means of a manual or automatic suction-discharge device, built into an automated device or not. Lastly, it relates to a sample drawing device, such as a pipette, and a device for detecting the free surface of a biological sample or a solid. Regardless of the device in question, it may be either manual or automatic, or built into an automated device or not.

This is a new method for detecting the level of a biological liquid in a specimen holder or test tube, particularly necessary on an automatic analyzer.

2. Description of the Related Art

The prior art shows that numerous methods are often used on other automated devices.

These methods may be electric.

Firstly, a reusable metal needle may be used which acts as an electrode, the second electrode being the liquid in which the needle will enter. When the needle comes into contact with the biological sample, a variation in impedance, capacitance or resistance, after amplification, triggers the shut-down of the needle lowering motor.

Secondly, a cone or conductive tip may be used which can be clipped on and thus disposed of after each sampling by the pipette associated with the cone. The latter are made of a plastic material which is loaded with carbon particles. The electrical connection is ensured by the cone gripping device which must be metallic.

Thirdly, other systems operate by adding to the needle or sampling cone, two electrodes placed on each side of the needle or cone, and ensuring electrical current conduction when these electrodes come into contact with the biologic liquid. This latter variant exhibits the major defect of contaminating the electrodes each time they come into contact with a new biologic liquid, thereby requiring the addition of a decontaminating washing system.

These methods may be optical.

Firstly, a camera may be used which displays the liquid level and when the needle comes into contact with the liquid.

Secondly, an optoelectronic system may also be used, featuring a photodetector which detects the liquid level and the needle's contact with the liquid or the sampling point in the liquid.

According to all embodiments of the sampling means, associated with electronic or optical means, during the sampling operation, the needle or sampling tip enters the biological sample to be drawn. If the needle or tip enters too deeply into the liquid of the sample, there is, on the one hand, a risk of contamination from the exterior of the needle and, on the other hand, an "overdosing", that is to say that the quantity of biological liquid having wetted the external wall of the needle or tip will be fully or partially released after transfer into the specimen holder, thereby distorting the exactness of the distributed dose.

There are, however, techniques which allow the tip used not be contaminated by the sampled liquid.

These methods may be acoustic. The patent U.S. Pat. No. 4,846,003 describes a detection system which uses an acoustic characteristic emitted by a speaker and received by a microphone. The value measured is established by the acoustic impedance.

Other documents, such as EP-A-0.341.438, U.S. Pat. No. 5,723,795, and EP-A-0.571.100, recommend the usage of pressure sensors. This system consists in detecting a pressure fluctuation, as soon as the free end of the tip comes into contact with the surface of a liquid.

Nevertheless, the sensors of these devices are associated with constantly uniform and unidirectional air movements. They do not allow for the evaluation of the numerous characteristics according to the present invention. The purpose of the invention is not only to detect a liquid or solid surface, a tip defect, and/or a leakage problem. The purpose of the invention includes the following:

to detect and to distinguish between the presence of a bubble or foam at the surface of a liquid sample to detect or to draw, to detect a bubble, a solid impurity or an impurity having a different density in said sample;

to distinguish between a bubble (when detected) from foam (or foam from a bubble) at the surface of a liquid sample to detect or to draw;

to distinguish a bubble (when detected) from a solid impurity or from an impurity having a different density in said sample. Moreover, the present invention may as well be used as a viscometer, as there is a relationship between the duration of the sampling operation, the vacuum pressure created within the pipette and measured by a pressure sensor, and the viscosity of the liquid sampled. The applicant has also filed a patent application, under number FR98/01376 dated Feb. 2, 1998, relating to: "Procédé et dispositif de mesure de la viscosité d'un liquide et utilisation d'une pipette comme viscosimètre" (A process and device for measuring the viscosity of a liquid and the usage of a pipette as a viscometer). The contents of this patent application are incorporated in this invention.

Furthermore, current techniques, which prevent the needle or sampling tip from entering too deeply into the biological sample to be drawn, require the use of complex means (camera, carbon tips, etc.) for detecting the free surface of the sample; means which are thus expensive and make their distribution on the market limited.

The invention thus aims at solving all of these problems by offering devices which are easy to use. Such devices assist in doing away to a significant degree with problematic electrical contacts, with the use of non-conductive disposable tips which are much less costly and less critical to manufacture, and with the reuse of a sensor already available for detecting needle clogging.

BRIEF SUMMARY OF THE INVENTION

To this end, the present invention concerns a method for drawing a biological sample by means of a suction-discharge device, such as a manual or automatic pipette, built into an automated device or not, characterized in that it includes:

actuating a means causing a pressure variation and/or a flow of air within the device, positioning the lower free end of said suction-discharge device in such a way that it is flush with the free surface of the biological sample, measuring overpressure, due to the flushness of the lower free end of said device with the free surface of the biological sample, and drawing a quantity of said sample by suction using the device.

The present invention also concerns a method for detecting the free surface of a biological sample or of a solid by means of a manual or automatic suction-discharge device, built into an automated device or not, characterized in that it includes:

actuating a means causing, within the device, a pressure variation and/or air flow which corresponds to the idle state of said device, and detecting a pressure, within the suction-discharge device, which is different from the pressure variation or air flow when idle, this pressure corresponding to the position in which the lower free end of said device is flush with the free surface of the sample or solid.

In all cases, the suction-discharge volume variation ranges from a few nanoliters (nl) to a few microliters (μl), and/or the constant pressure variation, otherwise referred to as frequency, ranges from a few Hertz to a few hundred Hertz (Hz).

In all cases, the air flow ranges from 10 to 50 μl per second, and preferably from 20 to 30 μl per second.

Furthermore, a pressure variation different from the pressure variation normally created by the means that generates this variation, before coming into flush contact, allows the following to be detected:

a sampling tip anomaly, the presence of said tip on the pipette, and/or the presence of at least one air bubble in the sample, or on the surface of the sample.

Likewise, a pressure variation in relation to the measured pressure, when the air flow is created, allows the following to be detected:

at least one air bubble, in the case where a pressure plateau is detected following an initial pressure variation, or a free surface of a liquid, in the case where a second pressure variation follows the first pressure variation, or a surface of a solid in the case where there is only a pressure increase.

A pressure variation must be interpreted as consisting of a pressure increase followed by a pressure decrease or by a pressure decrease followed by a pressure increase, which generates a peak.

The invention also concerns a device for drawing a biological sample, such as a manual or automatic pipette, built into an automated device or not, characterized by the fact that it features:

at least a means for creating a pressure variation or an air flow within the device at rest, at least a pressure sensor for measuring, on the one hand, the pressure variation at rest or a pressure different from this pressure variation or, a pressure different from the pressure created by the air flow within the device, on the other hand, and means for analyzing measurement parameters from the sensor(s) to enable the sampling operation to take place, when the lower free end of said suction-discharge device is flush with the free surface of the biological sample.

According to a special embodiment, the device used to detect the free surface of a biological sample or a solid is manual or automatic, and is built into an automated device or not; it features:

at least a means for generating a pressure variation or an air flow within the device at rest, at least a pressure sensor for measuring, on the one hand, the pressure variation at rest or a pressure different from this pressure variation, or a pressure different from the pressure created by the air flow within the device on the other hand, and means for analyzing measurements from the sensor(s) used to detect when the lower free end of the suction-discharge device becomes flush with the free surface of the biological sample or a solid.

The means for creating a pressure variation consists of a flexible tube which can be compressed and decompressed regularly by any reciprocating movement type mechanism, such as a cam or crank associated with a motor.

The means creating the air flow consists of the pipette piston, when it ejects the air outside said pipette.

The lower free end of the device is made up of a disposable tip.

BRIEF DESCRIPTION OF THE DRAWINGS

The enclosed drawings are provided for informational purposes only and do not depict a preferred embodiment of the present invention.

Finally.

DETAILED DESCRIPTION OF THE PREFERRED EMBODIMENTS

In the text that follows, the term "flush with" should be understood as being an equivalent to "entering into contact with". A tip being more or less equated with a hollow tube, the flushness is thus synonymous with contact between the lower free end of the tip and the free surface of the biological sample to be drawn or possibly the surface to be detected, without the outside side walls of said tip being "soiled" by the sample. In fact, the interior or exterior side walls are or are not "soiled", prior to the sampling operation, depending on whether said biological sample is a wetting or a non-wetting liquid. The contact must be able to allow sampling to take place without creating bubbles of air or any other gas and by "soiling" the outside of the tip as little as possible.

In order to facilitate the understanding of FIGS. 2 to 4 and 7 to 9, it should initially be noted that the time runs from right to left and that the position above the baseline 21 corresponds to a negative pressure and that the position below the baseline 21 corresponds to an overpressure.

Figure 1:
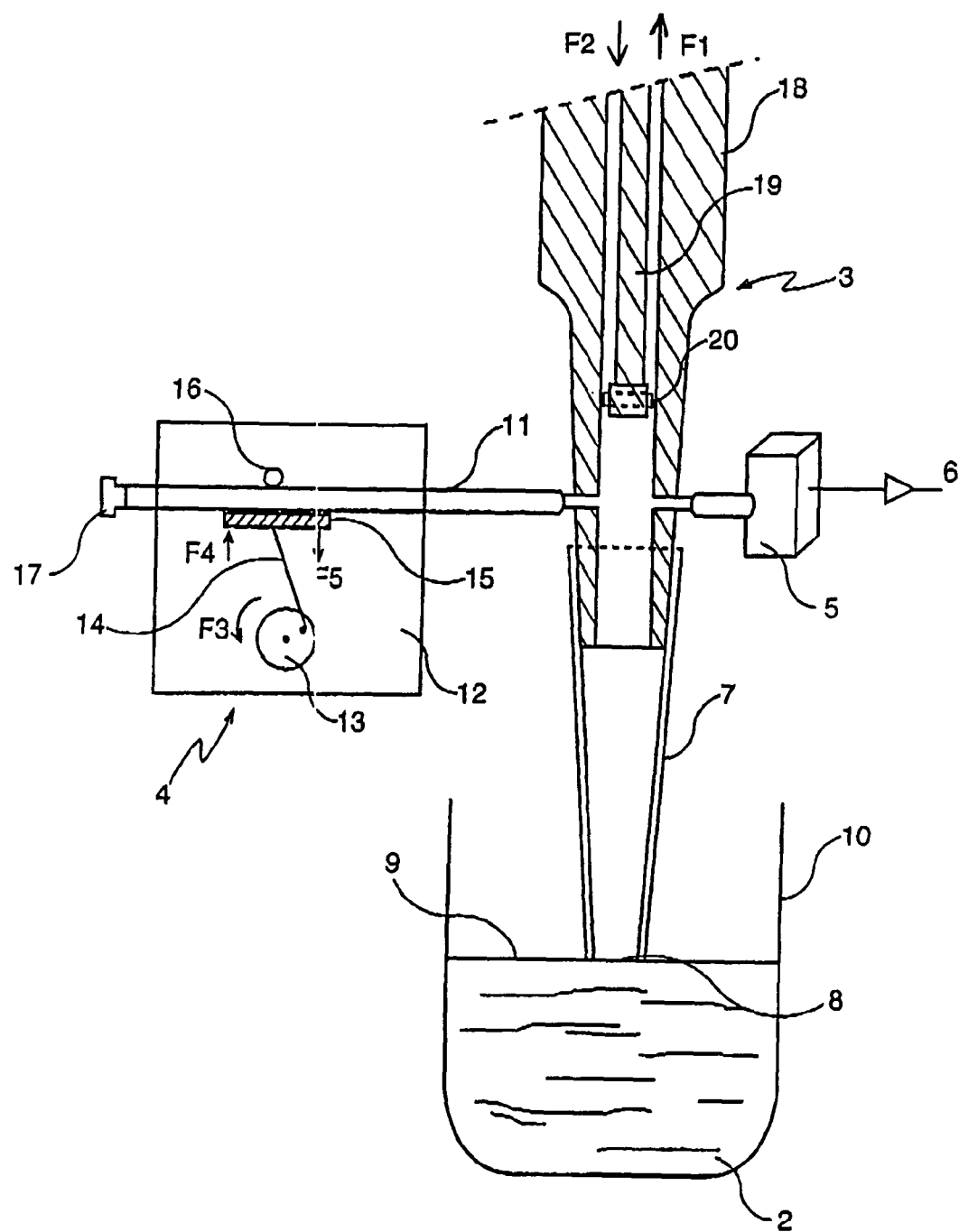
FIG. 1 represents a diagrammatic view of a sampling or level detection device (free surface) according to the invention which enables the implementation of a sampling or detection method and uses a means which creates a pressure variation.

According to FIG. 1, a sampling device 1, according to the present invention, is well represented.

This device 1 is essentially comprised of a pipette 3 which enables the sampling of a biological sample 2 contained inside a specimen holder 10.

The pipette 3 is essentially comprised of an external body 18 containing a piston 19. The mobility of the piston 19, according to F1 and F2, inside the body 18 of the pipette 3, allows both the suction and discharge, respectively, of the liquid (2) to be sampled. Of course, the device is fitted with a sealing joint 20 between the piston 19 and the body 18 of the pipette 3.

Also, as common practice dictates, the free end of the body of the pipette 18 is fitted with a tip 7, also referred to as a cone or sampling funnel.

One of the essential problems when taking a biological fluid sample 2 is based on the fact that the quantity drawn varies depending on the wettability properties of the liquid 2. The variability of the volume sampled, even if it is low, may have consequences on the results of the analyses. There is thus a real need to remove the differences in the volumes drawn when the biological sample 2 is a wetting liquid or not.

In order to accomplish this, the present invention proposes to associate the pipette 3 previously described with a means which enables a pressure variation to be created, referenced globally as 4 in FIG. 1. This pressure changing means 4 is also associated with a pressure sensor 5 which measures the pressure and the pressure variations when the pipette 3 is being used. Of course, in order for these components to operate, means for analyzing measurement parameters 6 coming from the sensor 5 are needed to enable sampling in the optimal conditions which will be described below.

Figure 5:
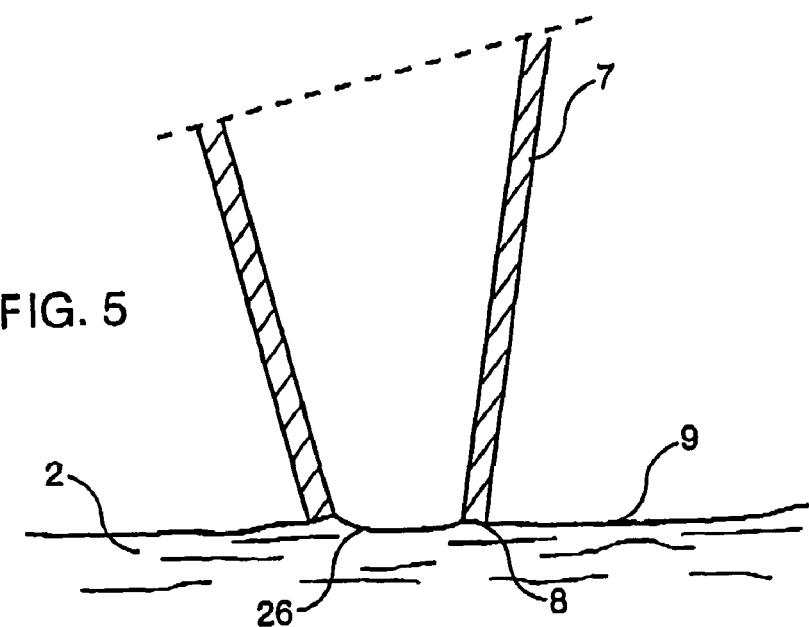
FIG. 5 represents a cross-sectional view at the level of the lower end of the tip which is flush with the surface of a non-wetting liquid.
Figure 6:
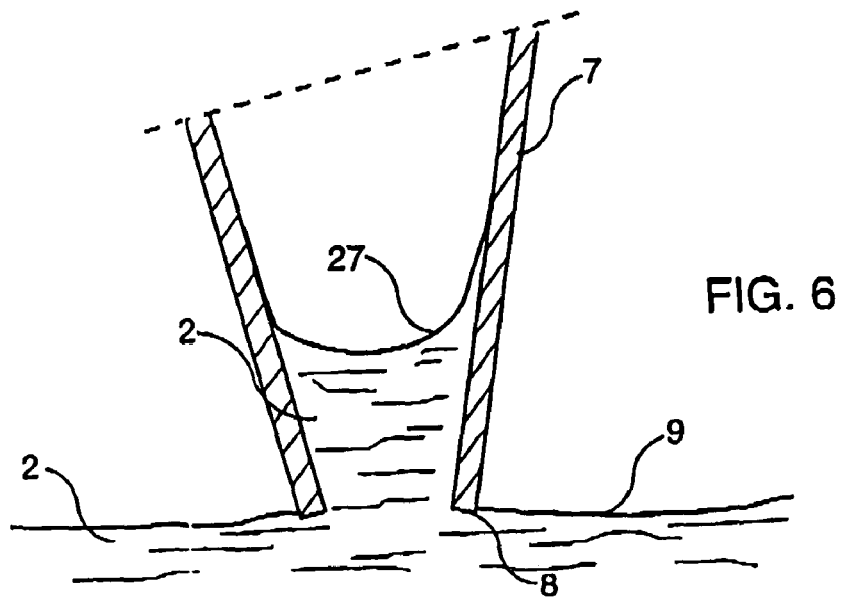
FIG. 6 represents a view which is identical to FIG. 5 in the case of a wetting liquid.

These optimal sampling conditions are those in which the lower free end 8 of the tip 7 is located on the free surface 9 of the biological sample 2 to be drawn, as is shown in FIGS. 1, 5, and 6. In this configuration, it is obvious that the outside surface of the cone 7 will not be "soiled" by the liquid being sampled 2. This characteristic enables an initial source of error to be avoided.

Furthermore, in reference to FIGS. 5 and 6, it can be seen that there is a large difference between the biological samples 2 to be drawn according to whether they are wetting liquids or non-wetting liquids, that is to say having the tendency to spread out on a surface when coming into contact with such liquids.

In the case of a non-wetting liquid 2 as shown in FIG. 5, the liquid 2 remains on the outside of the tip and the free surface 26 of said sample 2 within the pipette 3 does not enter into the pipette 3.

In the case of a wetting liquid 2, the liquid 2 enters into the tip 7, more or less deeper depending on the wettability of said liquid 2. The free surface 27 of the sample 2 is thus positioned within the pipette 3.

Figure 2:
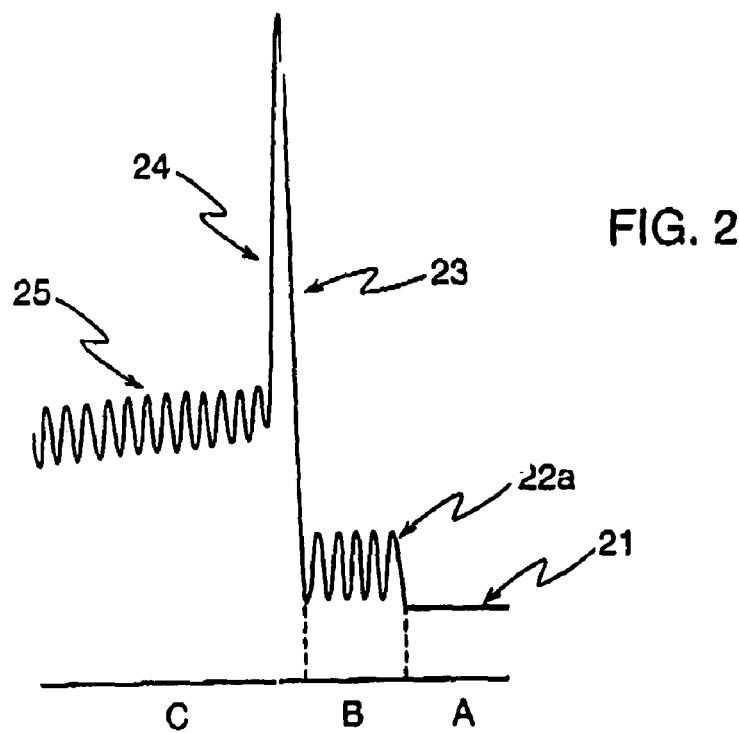
FIG. 2 represents a view of an electrical signal at the output of the pressure sensor as displayed by an oscilloscope, when used by a device according to FIG. 1 in the case of a non-wetting liquid.
Figure 3:
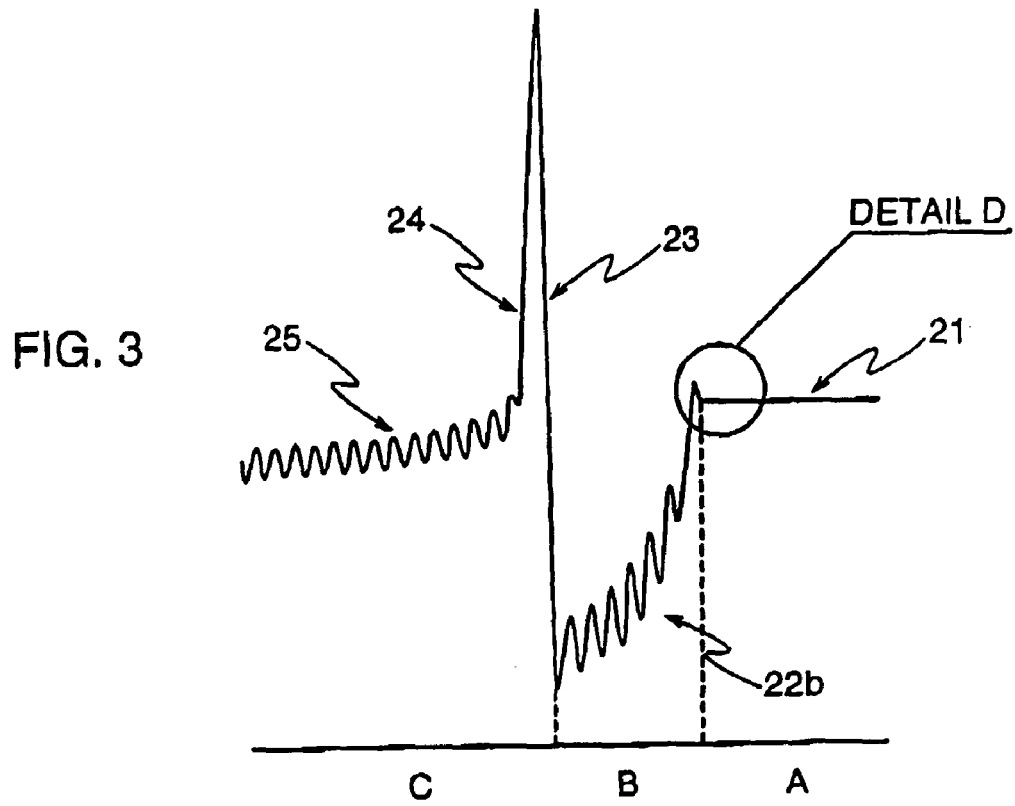
FIG. 3 represents a view identical to FIG. 2 in the case of a wetting liquid.

Of course, the curves of FIGS. 2 and 3, corresponding to the two possibilities of FIGS. 5 and 6 respectively, are modified according to the wetting or non-wetting properties of the biological sample 2. As such, the signal 22a, when the end 8 is in contact with the free surface 9 of a non-wetting liquid prior to suction, is different from the signal 22b, when the end 8 is in contact with the free surface 9 of a wetting liquid, also prior to suction.

The difference lies in the fact that the signal 22a is located above the baseline 21 corresponding to the atmospheric pressure while signal 22b is below this line 21.

The object of the present invention is thus also to detect the free surface 9 of a sample 2, whether it is wetting or non-wetting.

To accomplish this, the inside of the tip 7 is associated with both the pressure sensor 5 and a means creating a pressure variation 4. According to an embodiment represented in FIG. 1, the means creating a pressure variation 4 consists of a support 12 which may possibly be built into an automated device, which is not shown in the figures. This support 12 consists, for example, of the framework or the structure of the automated device.

This structure 12 serves as a support for a crankshaft 13 to which it is connected by a spin axis. The crankshaft 13 is also associated to one of the end of a connecting rod 14. The other end of this connecting rod 14 is connected to a pressure roller 15, the movement of which is alternating in the direction of F4 and F5 to enable the compression of a flexible tube 11 between the pressure roller 15 and an anvil 16.

The anvil 16 is in fact attached to the support 12 and cannot move, unlike the pressure roller 15. The flexible tube 11 has two ends; one end is closed off by a plug 17 while the other end is mechanically connected to the pipette 3. For that matter, the inside of the flexible tube 11 is in direct contact with the inside of the pipette 3 in the space defined by the body of the pipette 18, the piston 19 and the tip 7. It is thus easily understood that the motor, not shown in the figures, will rotate the crankshaft 13, as per F3, the movement of the pressure roller 15 will take place as per F4 then as per F5 to enable the compression, on the one hand, and the decompression, on the other hand, of the flexible tube 11 against the anvil 16. When the roller 15 moves as per F4, the tube 11 is pressed and a flow of air arrives via the pipette 3. When, on the contrary, the pressure roller 15 moves as per F5, the pressure exerted on the tube 11 is eliminated and said tube 11 may suck up again the air which was injected into the body 18 of the pipette 3. The average movement of the pressure roller 15 ranges from a few Hertz to a few hundred Hertz. The tube 11 is selected so that the volume displaced, that is to say drawn and discharged, ranges from a few nanoliters to a few microliters.

It can thus be easily understood, with reference to FIGS. 2 and 3, that the signal transmitted by the pressure sensor 5 is comprised essentially of three well-defined zones: A, B, and C.

In the case of zone A, the electric signal at the output of the sensor 5 corresponds to the position prior to contact between the end 8 of the tip 7 and the sample 2. In the case of zone B, the signal of the sensor 5 corresponds to the position after the end 8 comes into contact with the sample 2, although prior to suction by the pipette 3. In the case of zone C, the signal corresponds to the position after contact between the end 8 and the sample 2 has been established, although after suction.

Figure 4:
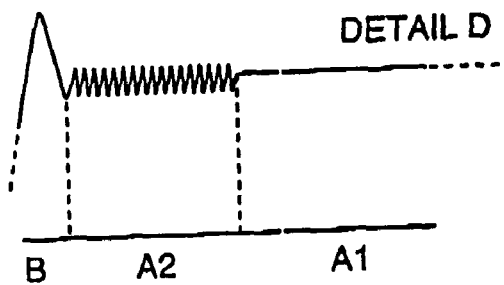
FIG. 4 represents detail D of FIG. 3.

The signal in zone A is more complicated and consists of two zones A1 and A2, as shown in FIG. 4 which is a detail of FIG. 3. This breakdown also exists in the case of FIG. 2. Zone A1 corresponds to an atmospheric pressure measurement signal before the means 4, which generates a pressure variation, is put into operation. Zone A2 corresponds to an atmospheric pressure measurement signal after means 4, which generates a pressure variation, was put into operation. As such, the signal A1 is completely flat, while signal A2 demonstrates a slight amplitude caused by the movements of air as per F4 and F5.

In this manner, this technique enables the free surface 9 of a biological sample 2 to be detected regardless of the wetting characteristics (wetting or non wetting) of this sample 2.

The present invention thus relates to a method for drawing a biological sample 2 by means of a suction-discharge device, and a method for detecting the free surface 9 of a biological sample 2 by means of this same device, if possible. Finally, it concerns a device 1 for drawing a sample 2, such as a pipette 3, and a device for detecting the free surface of a biological sample.

These new methods and devices for detecting the level of a biological liquid in a specimen holder or test tube are particularly necessary for automatic analyzers.

In fact, when a sampling tip, needle or cone 7 comes into contact with a liquid 2, such as a serum or biological reagent, a slight overpressure is generated inside the tip 7. This is related to and dependant on the wettability of the tips 7, as well as the hydrostatic tensions of the various liquids sampled 2.

This increase in pressure, which is typically in the range of a few hundreds of microbars, is detectable using a sensor 5, for example, derived from standard commercial micro-machining technology applications. This microcapillarity phenomenon exists in the majority of biological liquids. However, certain slightly wetting liquids can fault the concept described above, as this liquid, as its name indicates, does not spontaneously enter into the sampling tip 7, and does not generate the slight overpressure required for the sensor 5 to function, and thus the reason behind the search for a liquid presence indicator.

The invention thus consists in injecting a flow of air into the air space trapped in the sampling tip 7. This flow of injected air, disturbing the precision of the sampling mechanism, is instantaneously sucked back out. A come-and-go system with a small quantity of air of approximately a fraction of a micro-liter is thus obtained. Refer to the curves in FIGS. 2 to 4 and 7 to 9.

This quantity is small enough in terms of quantities of air in movement, providing the correct volumetry necessary to pump the liquid dosage. This air flow is injected then sucked back out at sufficiently fast speed so that it has no effect on the displacement of liquid inside the opening of the sampling tip; in this manner, the suction/discharge cycle is carried out in just a few milliseconds. The pressure sensor 5 reacts at a speed in the order of 100 microseconds. At this speed, the liquid is not able to enter the tip 7.

The usage of this system is particularly interesting in the case of a liquid having low surface tension which enters into contact with the opening of the sampling tip 7. Furthermore, this invention enables, more appropriately, the geometry of the cone's end to be qualified whereas if this end has asperities caused, for example, by poor molding, the micro flow of air entering and exiting is disturbed, which results in a modification of the pressure variation which is easily detected by this same pressure sensor 5.

The flows and return flows of air are generated by a micropump 4, operating on the crank connecting rod principle, and compressing a silicone microtube 11 whose interior capillary has a small diameter, in the order of a few tenths of a millimeter.

With each motor revolution, the tube 11 is alternately distorted and restored to its initial shape, thereby generating a flow and backflow of air, respectively. These flows and backflows of air are transmitted, via the tube, to the internal chamber of the sampling tip 7.

In this respect, one of the two ends of the tube 11 is connected to said internal chamber of the sampling tip 7. The other end of this tube 11 is blocked by a plug 17. The pressure sensor 5 is in direct contact with the air passage of the pipette's pumping mechanism; the pipette is of standard type operating as per the known cushion displacement principle.

According to an example shown in FIG. 2, the different types of electronic signals resulting from the micro-pressure sensor 5 are standard and can be used by any microcomputer programmed to detect a signal of a few millivolts becoming instantaneously (in a few milliseconds) a few hundred millivolts.

It is also possible to vary the flow and backflow air volume, for example from a few fractions of a microliter to a few microliters, and to vary the pulse frequency, enabling said air volume to be pulsed from a few tens of Hertz to a few hundreds of Hertz, without departing from the scope of the invention.

Likewise, the air flow may be generated by other systems such as a hermetic micro-speaker whose acoustic membrane acts as a pump membrane. The hermetic cavity placed against the speaker traps a small volume of air which is then injected into the upper part of the sampling tip 7.

In the same way, any type of piezoelectric system capable of advantageously fulfilling the pumping function may be used.

The invention described above is used as a system for detecting the level of a liquid to be sampled 2. There may also be another functionality associated with the total blockage of the sampling tip 7, when the end of said tip comes into contact with the liquid. This system still enables a partial blockage of said sampling tip 7 to be detected, for example when a biological liquid 2 is dried or crystallized at one of the end or inside this sampling tip 7.

Other functions are possible with this device.

Leak detection at the junction between the sampling cone and the sampling mechanism can thus also be foreseen. If there is a leak at this point, the negative pressure signal collected at the sensor terminals (pressure/negative pressure sensor) 5 is totally different as the negative pressure peak is weaker, and the plateau associated to the height of the water column constantly falls over time. The slope of this plateau directly reflects the magnitude of the leak.

Bubbles can also be detected as the biological liquid is being sucked up as the non-progressive negative pressure is detected by the sensor. In this case, the sole negative pressure peak is broken, 28 in FIG. 9, and several peaks (the number of which corresponds to the number of bubbles passing by the opening of the sampling tip) can be observed. The pressure balancing plateau is also inconstant.

A tip 7 which is improperly emptied can also be detected. Thus, during the sampled liquid ejection cycle, the overpressure generated by the pipette's 3 ejection mechanism, if it is too fast or if the liquid displays unfavorable wettability characteristics, will lead to the presence of a certain quantity of non-ejected liquid on the internal walls of the sampling tip 7; this will thus result in a distributed under-dosage. In this case, the invention is able to detect the formation of a coalescence of the liquid; this coalescence generates at least a ring of liquid which behaves like a fragile membrane. The flow and backflow of the volume of air ejected in the tip 7 is thus disturbed, which results in a very weak pressure variation which is detected by the pressure sensor 5. At the same time, if said tip 7 does not enter the liquid to be sampled 2, it can be deduced that the sampling tip 7 was not perfectly emptied. In this case, the section ejection cycle cannot be undertaken.

It is also possible to detect the presence of a tip as in the presence of an empty tip, without liquid contact, an alternating wave generated by the small volume of air injected is detectable by the pressure sensor 5, while when this tip is absent, this signal does not exist. Furthermore and advantageously, if the pump 4 operates continuously and there is no tip 7 fitted on the pipette 3, there is no signal. Such a signal can only appear when the tip 7 is present. In this manner, a new tip 7 presence detection function is made.

Partial blockage can also be detected. The blockage detection processes are known and form the subject of numerous patents dealing with the total blockage of a needle or a sampling tip. The present invention proposes a device which operates only on the air cushion above the column of liquid, which considerably increases the sensitivity of the pressure sensor used. In this manner, a small obstruction of the cone's entrance results in a small pressure variation which, compared to an unobstructed cone signal, exposes a partial blockage.

It is also possible to qualify the hydrostatic forces. Owing to its extreme sensitivity, the device according to the invention enables the wettability qualities of the internal surfaces of the sampling cones 7 and the surface tensions of the various biological liquids to be advantageously monitored. Actually, the negative pressure peak increases as the liquid's wettability decreases and as the internal surface of the cone 7 is water-repellent. Using a set of master curves stored in the process management computer, the biological liquids may be qualified on these new criteria.

It is even possible to define the cone or tip. On a biological analyzer, the quantity of sampling tips 7 is very important because, during a very short time, the entire sample passes by its capillary opening. The speeds of the biological liquids are locally fast, which explains that a small deformation of the end of the sampling cone modifies the speed of the liquid, and thus the instrument's expected volumetric precision. Our invention makes a small variation in the flow of the biological liquid perceptible, as the pressure difference measured by the pressure sensor 5 will be compared to master curves stored in the computer.

The sampling speed may be controlled. In this manner, the extreme sensitivity of the invention, associated with the typical negative pressure/overpressure curves allow small changes in sampling speed to be detected, which is very important in the final volumetric precision drawn. Of course, these elements are managed by the computer of the instrument, which is well-known in the art.

Finally, it is possible to check for leaks in the sampling mechanism. The device according to the present invention is judiciously placed inside the pump body 11; in this manner, it is possible to thoroughly check the seal of all the parts which contribute to the correct operation of the system, with the sampling cone 7 not fitted. The inspection procedure may be performed prior to starting the analyzer by artificially blocking the end of the tip holder. An overpressure is generated by the pumping mechanism 4, within the pipette 3, and the pressure sensor 5 monitors seal integrity at this generated pressure for an extended period of time, for example one minute.

The invention thus concerns a method for detecting the level of a liquid by pressure variation using a pressure sensor 5, associated with a pulsed air flow, obtained by injecting then sucking out a small volume of air.

The air flow frequency ranges from a few Hertz to a few hundred Hertz.

The volume of pulsed air is a quantity varying from a few nanoliters to a few microliters.

As far as the presence of air bubbles in the sample 2 is concerned, the curves 7 to 9 show this problem clearly.

Figure 7:
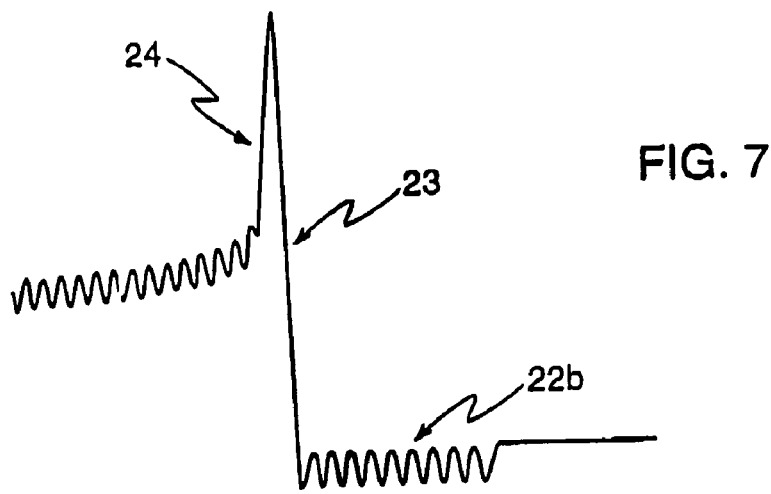
FIG. 7 represents a view of a conventional electrical signal at the output of the pressure sensor as viewed by an oscilloscope.

In this manner, FIG. 7 represents a conventional electrical signal at the output of the pressure sensor 5 displayed by an oscilloscope. This signal can be broken down as follows.

Firstly, there is a baseline 21 which corresponds to the atmospheric pressure when the end 8 is positioned above the free surface 9. The signal 22b corresponds to the fact that the end 8 is in contact with the free surface 9 of a wetting liquid 2 prior to suction. Then, a negative pressure 23 appears, caused by the raise as per F1 of the piston 19 causing the sample 2 to rise in the tip 7. Then, the negative pressure 24 decreases due to the stabilization of the position of said sample 2 inside said tip 7. Finally, a balancing negative pressure 25 is established at a corresponding level of the liquid column 2.

Figure 8:
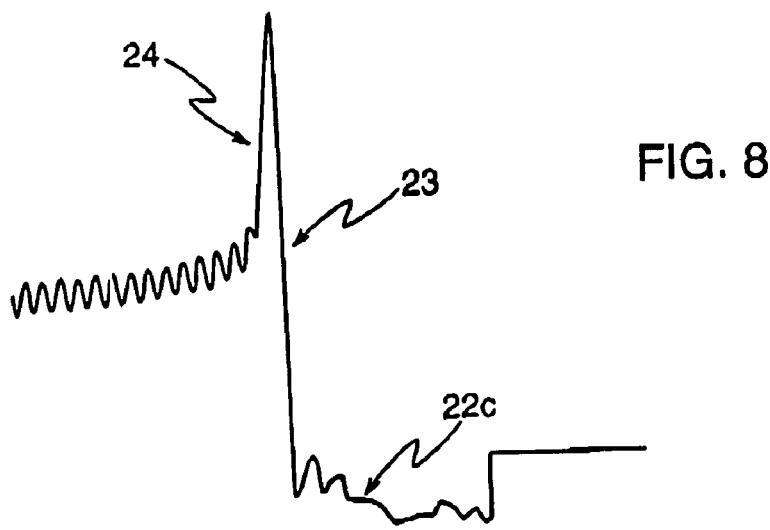
FIG. 8 represents a view of an electrical signal which is identical to that of FIG. 7 although disturbed by the presence of many small bubbles on the surface of the sample creating foam.

FIG. 8 represents an electric signal which is identical to that of FIG. 7 although disturbed by the presence of many small bubbles at the surface of the sample, forming foam. As a result, in zone B, the variations created by means 4 are much more regular 22c. This is related to the fact that the pressure sensor 5 alternatively detects the presence of liquid 2 and air. In this case, the signal reflects the references 21, 23, 24 and 25 explained above, although reference 22b is replaced by reference 22c.

Figure 9:
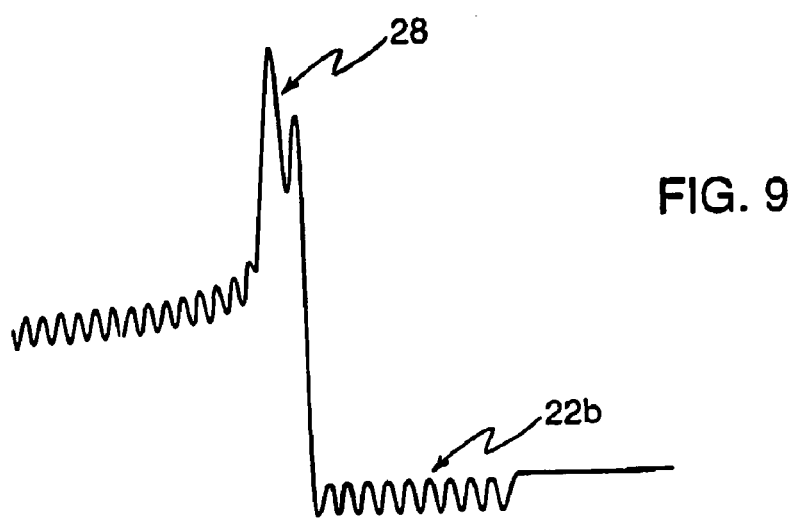
FIG. 9 represents a view of an electrical signal which is identical to FIG. 7 although disturbed by the presence of an air bubble inside the sample; an air bubble which is drawn in by the suction-sampling device.

Finally, FIG. 9 represents a view of an electric signal which is identical to FIG. 7 but also disturbed by the presence, inside the sample, of an air bubble which is sucked in by the suction-discharge device at the zone C level. This curve shows references 21, 22b, and 25, although references 23 and 24 are absent as they are replaced by a negative pressure 28 of the sample 2 in the tip 7 which is disturbed by an air bubble.

This invention enables leaks between the cone and the pipette to be detected, but also the presence of gas bubbles in the sample during the sample drawing operation, cones imperfectly emptied, cone presence, and the partial blockage of a cone by a biological reagent. The invention also enables the qualification of hydrostatic forces (surface tension/wettability), the qualification of the cone (geometry/molding of the end), the speed checking of the sampling device, and checking for leaks in the mechanism of said device.

According to a second embodiment, the pipette 3 may have a structure which is simpler that the pipette shown in FIG. 1. In this embodiment, represented in FIG. 10, there is no means causing a pressure variation 4. There is only, in lateral position (position not mandatory), the pressure sensor 5 which is itself connected to a measurement parameters analysis means 6.

Figure 10:
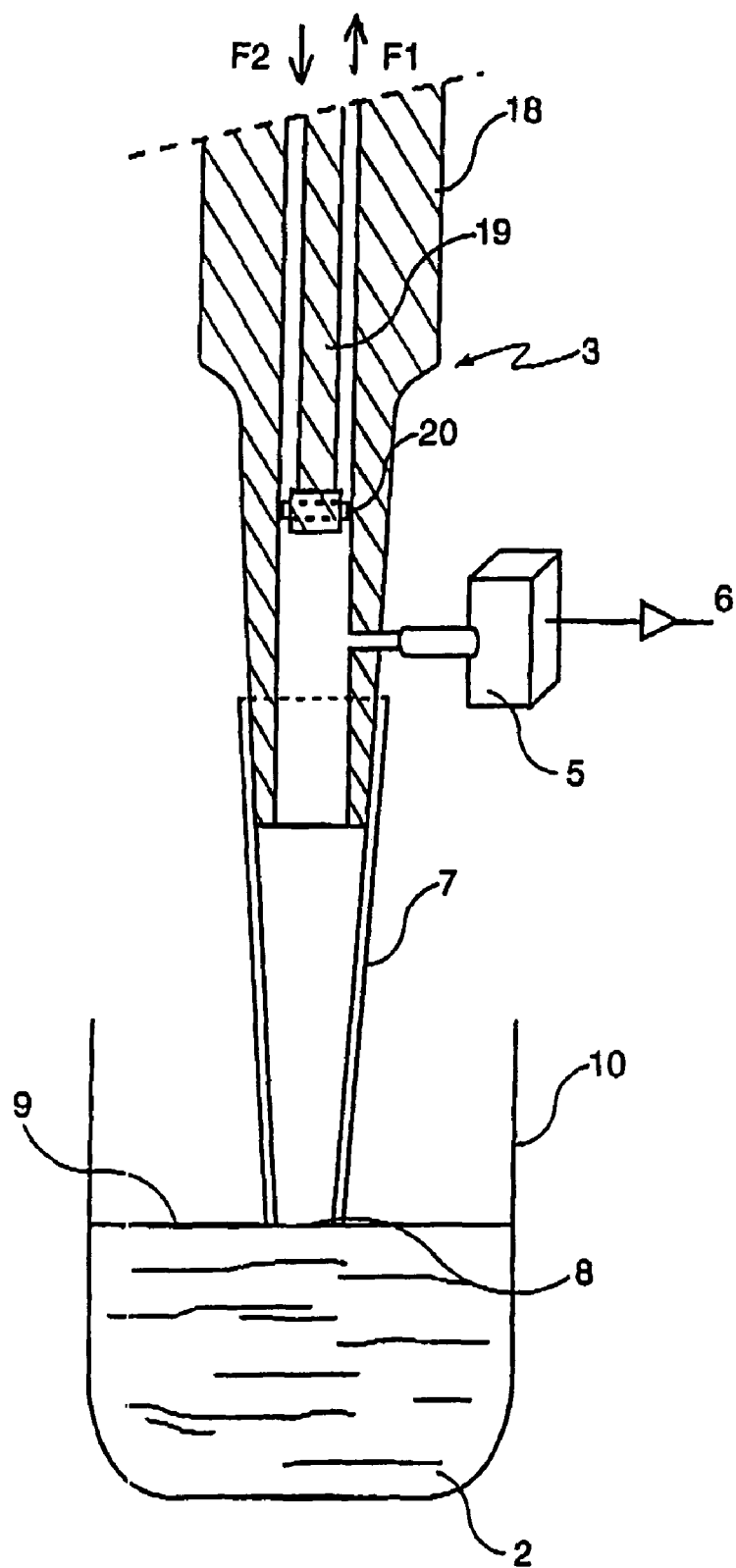
FIG. 10 represents a diagrammatic view of a sampling or level detection device according to the invention which enables the implementation of a sampling or detection method and uses a means that creates an air flow.

In fact, the object of this invention resides in the use of the piston 19 to create a continuous and constant flow of air at the tip 7. To accomplish this, the piston 19 is raised to its maximum position as per F1 prior to usage. As soon as the pipette 3 is actuated by an automatic or manual movement that bring it closer to the level to be detected, as shown in FIG. 10, the piston moves in direction F2 in order to expel the air contained in the pipette 3 and said tip 7 to the outside. This air will thus be expelled at the lower free end 8 of said tip 7.

As long as the free end 8 does not come into contact with a liquid or solid surface, it is obvious that the pressure measured by the sensor 5 will not be constant. Nevertheless, as soon as the end 8 is close to a surface 9, the latter will tend to completely obstruct the end 8 and thus increase the pressure inside the pipette 3 and the tip 7. Measuring this pressure variation is the key to detecting the presence of a surface 9.

Figure 11:
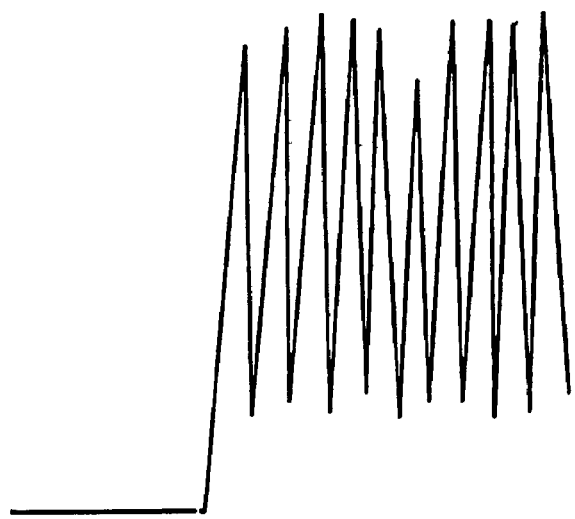
FIG. 11 represents a view of the electrical signal at the output of the pressure sensor as viewed by an oscilloscope, when using a device according to FIG. 10, the tip entering into direct contact with the free surface of a liquid.
Figure 12:
FIG. 12 represents a view identical to FIG. 11 in the case where the tip comes into indirect contact with the free surface of a liquid as bubbles are present.
Figure 13:
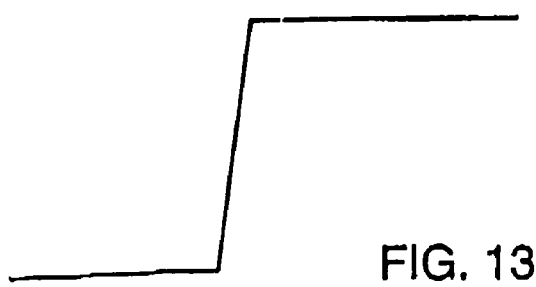
FIG. 13 represents a view identical to FIGS. 11 and 12 in the case where the tip comes into contact with the free surface of a solid.

As shown in FIGS. 11, 12, and 13, depending on the signals transmitted by the pressure sensor 6, it is possible to determine the type of liquid or solid located below. In the case of a solid of course, it is quite possible to perform a detection measurement of the surface which is vertical as is the case with solids.

As per FIG. 11, we note that the signal is first horizontal, to the left of the figure, and corresponds to the atmospheric pressure or, in any case, to the pressure inside the pipette 3 and tip 7 under the effect of the air flow created by the piston 19. At a given moment, the straight line is transformed into a curve which increases and forms a number of successive peaks. This curve corresponds to the fact that the free end 8 of the tip 7 is at the level of the free surface 9 of the liquid to be detected 2. The peaks thus correspond to the creation of air bubbles within the liquid.

Obviously, if the contact surface had been a solid, an increase in pressure would have occurred, followed by a plateau of high pressure showing that bubble formation was not possible. This is clearly shown in FIG. 13.

However, in the case of FIG. 12, there are two initial peaks which are characteristic as they are followed by a descending plateau ending substantially at the atmospheric pressure level. Each of these peaks, followed by a plateau, corresponds to the presence of an air bubble which entails an increase in pressure at the beginning, then a decrease in pressure corresponding to the expansion of the bubble and finally to a return to the atmospheric pressure once said bubble has burst. In the special case of FIG. 12, it is thus easily understandable that the tip 7 is driven by a very weak vertical descending movement which allowed it to come into contact with an initial bubble, to expand it, burst it, then come into contact with a second bubble, to expand and explode it also and finally enter into contact with the liquid, which results, at the right of the curve in FIG. 12, in a number of successive peaks very similar to the peaks in FIG. 11.

According to the trace obtained by the oscilloscope, it is thus possible, via the pressure sensor 5, to determine the exact nature of the surface encountered. The surface may thus be a solid surface or a liquid surface. In this second case, two options exist, either there are bubble present on the free surface of the liquid or there are no bubbles on this surface.

It is also possible to detect the presence of bubbles on a solid surface. In this hypothesis, the signal transmitted by the sensor 5 will associate the signal of FIG. 12 with the signal of FIG. 13.

This invention can thus be easily used to detect surfaces. This is particularly interesting as it would preclude having to purchase systems which are much more complex such as optical detectors or lasers, which are much more costly.

REFERENCES

1. Sampling device
2. Biological sample
3. Pipette
4. Means creating a pressure variation or pump
5. Pressure sensor
6. Measurement parameters analysis means
7. Tip or cone or needle
8. Lower free end of the tip 7
9. Free surface of the sample 2
10. Specimen holder containing the sample 2
11. Flexible tube
12. Support
13. Crankshaft
14. Connecting rod
15. Pressure roller
16. Anvil
17. Plug
18. Body of the pipette 3
19. Piston of the pipette 3
20. Sealing joints
21. Baseline of the signal corresponding to the atmospheric pressure when the end 8 is positioned above the free surface 9
22*a*. Signal when the end 8 is in contact with the free surface 9 of a non-wetting liquid prior to suction
22*b*. Signal when the end 8 is in contact with the free surface 9 of a wetting liquid prior to suction
22*c*. Signal when the end 8 is in contact with the free surface 9 of a wetting liquid prior to suction, with foam on the surface of the sample 2
23. Negative pressure due to the raising of the piston 19 as per F1 causing the sample to rise in the tip 7.
24. Lowering of the negative pressure due to the stabilization of the sample's position 2 within the tip 7.
25. Balancing negative pressure at a corresponding level of the column of liquid 2
26. Free surface of the sample 2 within the pipette 3 in the case of a non-wetting liquid
27. Free surface of the sample 2 within the pipette 3 in the case of a wetting liquid
28. Rise of the sample 2 into the tip 7, disturbed by an air bubble
A. Electric signal at the output of the sensor 5 prior to contact with the end 8 and the sample 2
B. Signal from the sensor 5 after contact between the end 8 and the sample 2 prior to suction
C. Signal from the sensor 5 after contact between the end 8 and the sample 2 after suction
F1. Movement of the piston 19 in the body 18 of the pipette 3 allowing suction F2. Movement of the piston 19 in the body 18 of the pipette 3 allowing discharge
F3. Rotational movement of the crankshaft 13
F4. Compression movement of the tube 11 by the pressure roller 15
F5. Release movement of the tube 11 by the pressure roller 15

The invention claimed is:

1. A method for detecting a partial or total blockage at the level of a manual or automatic biological sample suction-discharge device which is built into an automated device or not, said method comprising:

actuating a means for creating a normal pressure variation due to a flow and backflow of air within a manual or automatic biological sample suction-discharge device, and measuring a pressure variation different from said normal pressure variation within the suction-discharge device, due to a partial or total blockage of a lower free end of said suction-discharge device.

2. The method of claim 1, wherein said means for creating a pressure variation comprises a pump which operates on the crank connecting rod principle.

* * * * *